(12) United States Patent  
Delzer et al.

(10) Patent No.: US 6,703,846 B2
(45) Date of Patent: Mar. 9, 2004

(54) SUPERABSORBENT POLYMER TARGETING REGISTRATION OF DRY FORMED COMPOSITE CORES

(75) Inventors: Troy Delzer, Butler, PA (US); Andrew Baker, Lawrenceville, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 10/046,206

(22) Filed: Jan. 16, 2002

(65) Prior Publication Data

US 2003/0132762 A1 Jul. 17, 2003

(51) Int. Cl.[7] .......................... G01R 27/26; A61F 13/15; B23Q 15/00; B26D 5/00
(52) U.S. Cl. ................. 324/663; 324/671; 604/358; 83/74; 83/364
(58) Field of Search ................. 324/663, 632, 324/637, 669, 535, 671; 83/76, 358, 360, 368, 74, 364, 365; 604/368, 358, 393; 156/353, 510; 264/118

(56) References Cited

U.S. PATENT DOCUMENTS

| 3,709,274 A | * | 1/1973 | Marek et al. ................... 83/13 |
| 3,829,764 A | * | 8/1974 | Bosisio ........................ 324/632 |
| 4,990,541 A | | 2/1991 | Nielsen et al. |
| 5,017,257 A | | 5/1991 | Murphy ....................... 156/268 |
| 5,082,627 A | * | 1/1992 | Stanbro ................... 422/82.01 |
| 5,281,207 A | | 1/1994 | Chmielewski et al. |
| 5,363,728 A | | 11/1994 | Elsner et al. .................. 83/23 |
| 5,450,777 A | * | 9/1995 | Molnar et al. ................. 83/98 |
| 5,451,882 A | | 9/1995 | Wakino et al. |
| 5,532,604 A | | 7/1996 | Nagata |
| 5,659,538 A | * | 8/1997 | Stuebe et al. ............... 700/124 |
| 5,807,366 A | | 9/1998 | Milani ........................ 604/368 |
| 5,863,288 A | | 1/1999 | Baker |
| 6,054,631 A | | 4/2000 | Gent .......................... 604/367 |
| 6,068,620 A | | 5/2000 | Chmielewski |
| 6,224,699 B1 | | 5/2001 | Bett et al. ..................... 156/64 |

* cited by examiner

Primary Examiner—Anjan K. Deb
(74) Attorney, Agent, or Firm—Hunton & Williams

(57) ABSTRACT

A system and method for adjusting the targeting of superabsorbent material in absorbent cores based on the timing of a cutting device are disclosed herein. After targeting superabsorbent material into a segment of absorbent core material, a first sensor is used to determine a change in concentration of superabsorbent material over the length of the segment, or alternatively, a rate-of-change in the concentration is determined. The change in concentration, or rate-of-change, can be interpreted as the timing of the superabsorbent material targeting. A second sensor is used to determine the timing of a cutting device used to separate the segment from the remaining absorbent core material. The timing of the targeting of the superabsorbent material can then be synchronized with the timing of the cutting device for targeting of superabsorbent material in subsequent segments of the absorbent core material.

63 Claims, 8 Drawing Sheets

SUPERABSORBENT POLYMER TARGETING REGISTRATION OF DRY FORMED COMPOSITE CORES

FIELD OF THE INVENTION

The present invention relates generally to systems and methods for manufacturing absorbent garment cores. More specifically, the present invention relates to a system and method for providing precise disposition of superabsorbent particles into an absorbent core.

BACKGROUND OF THE INVENTION

Disposable absorbent garments such as infant diapers or training pants, adult incontinence products and other such products typically are constructed with a moisture-impervious outer backsheet, a moisture-pervious body-contacting inner topsheet, and a moisture-absorbent core sandwiched between the liner and backsheets.

Cost-effective materials for absorbent cores that display good liquid absorbency and retention are desirable. Super-absorbent particles (SAP) in the form of granules, beads, fibers, bits of film, globules, etc., have been favored for such purposes. Such SAP materials generally include polymeric gelling materials that are capable of absorbing and retaining even under moderate pressure large quantities of liquid, such as water and body wastes, relative to their weight. The SAP particles typically are distributed within a fibrous web of fluffed pulp material, which may comprise natural or synthetic fibers. Such absorbent structures commonly are referred to as fluff pulp/SAP cores.

Superabsorbent materials generally include water-insoluble but water-swellable polymeric substances capable of absorbing water in an amount that is at least ten times the weight of the substance in its dry form. In one type of superabsorbent material, the particles may be described chemically as having a back bone of natural or synthetic polymers with hydrophilic groups or polymers containing hydrophilic groups being chemically bonded to the back bone or an intimate admixture therewith. Included in this class of materials are such modified polymers as sodium neutralized cross-linked polyacrylates and polysaccharides including, for example, cellulose and starch and regenerated cellulose that are modified to be carboxylated, phosphonoalkylated, sulphoxylated or phosphorylated, causing the SAP to be highly hydrophilic. Such modified polymers also may be cross-linked to reduce their water-solubility.

However, in order for superabsorbent materials to function, the liquid being absorbed by the absorbent core must come in contact with unsaturated superabsorbent material. In other words, the superabsorbent material must be placed in a position to be contacted by liquid. Accordingly, various wicking materials often are used to "wick" moisture to one or more desired locations of the absorbent core of the garment. Likewise, it often is desirable to "target" the superabsorbent material in the absorbent core by controlling the distribution of superabsorbent material to provide local regions of the absorbent core that have greater superabsorbent material concentrations than others. Such concentrations may be along one or more of the absorbent core's length, width and thickness. By targeting the superabsorbent material, superabsorbent material may be efficiently distributed in the absorbent core without reducing the ability of the absorbent core to absorb and store liquids. Since more superabsorbent material can be embedded in local regions of the absorbent core that are more likely to come into contact with body fluids or other liquids while less or no superabsorbent material is embedded in areas less likely to come in contact with body fluids or other liquids, less superabsorbent material generally is used overall, while the absorbent qualities of the absorbent core remain unaffected or may even improve.

In view of the benefits afforded by targeting superabsorbent material in absorbent cores, processes have been developed to target superabsorbent material during the manufacture of the absorbent core. However, due to inconsistencies and variances during these manufacturing processes, the timing of the targeting of the superabsorbent material into the absorbent core material relative to the timing of cutting devices used to cut the absorbent core material are haphazard at best. A small difference in frequency between the device used to target the superabsorbent material into the absorbent core material and the cutting device used to cut the absorbent core material into absorbent cores can amplify through successive iterations, resulting in a large error between an ideal targeting of the superabsorbent material and the actual targeting. This large error can result in the distribution of the superabsorbent material in an undesirable location of the resulting absorbent core.

Accordingly, an improved system and/or method for phasing the targeting of superabsorbent material would be advantageous.

SUMMARY OF THE INVENTION

It would be desirable to provide a system and method for depositing superabsorbent material into an absorbent core whereby the amount and position of the superabsorbent material can be controlled with relative accuracy. It also would be desirable for such a system and method to be able to deposit particulate matter in a manner that fewer rejected products are manufactured due to variations in the manufacturing process. Additionally, it would be desirable for such system and method to be efficient, easy to operate, and capable of operating at high line speeds.

In accordance with at least one embodiment of the present invention, a system for synchronizing a targeting of superabsorbent material into absorbent core material by a targeting device with a cutting of the absorbent core material by a cutting device is provided. The system includes a first sensor to obtain a measurement of a change in a concentration of the superabsorbent material over a segment of the absorbent core material, wherein the measurement is representative of a previous timing of the targeting device. The system also includes a second sensor coupled to the cutting device to determine the timing of the cutting device. Additionally, the system includes a drive control coupled to the first sensor and the second sensor, where the drive control adjusts the timing of the targeting device, and wherein the timing of the targeting device is adjusted by the drive control based on a comparison of the previous timing of the targeting device and the timing of the cutting device.

DETAILED DESCRIPTION OF THE PREFERRED EMBODIMENTS

Figure 1:
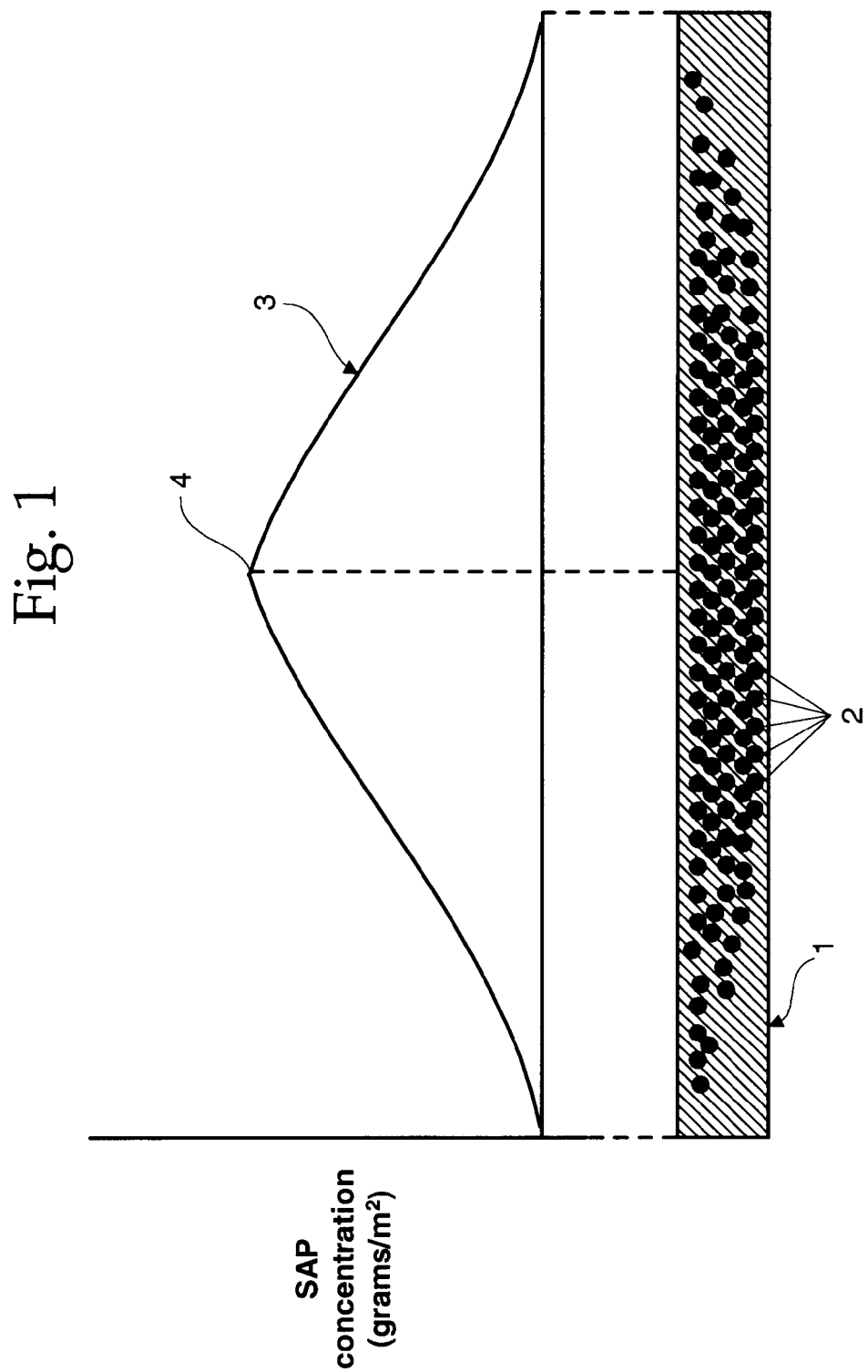
FIG. 1 includes a cross section of an absorbent core having a varying concentration of superabsorbent material in accordance with at least one embodiment of the present invention.

As used herein, the term "absorbent garment" or "garment" refers to garments that absorb and contain exudates, and more specifically, refers to garments that are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow.

FIGS. 1–10 illustrate a system and method for feedback control of the targeting of superabsorbent polymer (SAP) material into an absorbent core for use in an absorbent garment. After SAP material is targeted along the length of a section of continuous absorbent core material by a SAP targeting device, the concentration of the SAP material along the section is measured by a SAP sensor and provided to a drive control. In a preferred embodiment, the SAP concentration is measured by measuring the dielectric effect/capacitive effect caused by the SAP material. Accordingly, the absorbent core material preferably includes a low-density core material containing little or no pulp. The drive control compares the timing of the targeting of the SAP material using the measured SAP concentration, and based on the timing of a cutting device used to cut the absorbent core material into one or more absorbent cores, the drive control modifies the timing of the device used to target the SAP material into the absorbent core material. One advantage in accordance with a preferred embodiment of the present invention is that SAP material is more accurately targeted into an absorbent core. Another advantage is that SAP material is used more efficiently.

Referring now to FIG. 1, a cross section of an absorbent core of an absorbent garment having targeted SAP material is illustrated in accordance with at least one embodiment of the present invention. In a preferred embodiment, the absorbent core 1 comprises particles of superabsorbent polymer (SAP) material 2 distributed within a fibrous structure. Additional fibrous or particulate additives may be disposed within the absorbent core 1 to add to the core's strength and SAP efficiency or to otherwise enhance the performance of the garment. The absorbent core 1 may be partially or wholly surrounded by a tissue layer or other additional layers may be added to provide further benefits.

Certain fibrous materials preferably are used to form the fibrous structure of the absorbent core 1. These fibrous materials maintain high SAP efficiencies when the SAP concentration is in the range of about 50–95%, more preferably about 60–90%, and most preferably about 75–85%. For example, the fibrous structure of the absorbent core 1 may be made with tow fibers, cellulose acetate fibers, rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, blends of the foregoing materials, and the like.

Of the foregoing, cellulose acetate is the most preferred material for use as the fibrous structure. In addition, rayon, Courtauld's LYOCELL, polyacrylonitrile, cotton fibers and cotton linters have similar properties to cellulose acetate and are alternatively preferred. The remaining fibers, surface-modified polyolefin/polyester bicomponent fibers, and surface-modified polyester/polyester bicomponent fibers are also believed to be effective as a fibrous structure or as fibrous additives. In addition, the use of such fibers enables the production of ultra low density absorbent cores, when compared to absorbent cores prepared by dispersing SAP particles in fluff. The reduction in density is largely attributable to the reduced weight of the fibrous structure. Additionally, such fibers generally exhibit a relatively insignificant dielectric effect in comparison with the dielectric effect caused by SAP particles. As a result, the variations in the fibrous structure generally do not significantly impact the overall dielectric effect of the absorbent core.

The fibrous component of the absorbent core 1 preferably is comprised of at least one tow fiber, and most preferably is a crimped tow of cellulose acetate or polyester. Before making the absorbent core 1 that includes a tow fiber, the tow fiber typically is unwound and opened, and then cut at various lengths to provide a fibrous mass of material. Skilled artisans are aware of techniques available to open tow fibers and form the opened fibers into a fibrous mass. Absorbent cores of this type generally are known in the art, and exemplary absorbent cores are described in U.S. Pat. No. 6,068,620 and U.S. Pat. No. 5,281,207, both issued to Chmielewski, and U.S. Pat. No. 5,863,288, issued to Baker, the disclosures of each of which are herein incorporated by reference in their entirety and in a manner consistent with this disclosure.

In addition to the tow material, other fibrous components also may be used. For example, additional tow fibers (different from original tow fiber), or a low-density roll good made in a separate process may be used to form absorbent core 1. Conventional fluff or pulp also may be used together with the tow fibers. Still further yet, the fibrous component could also be a carded web formed on-line. Optionally, it is advantageous to introduce from about 1–5% of a thermally bondable fiber into the fibrous component of the absorbent core 1 for wet strength and core stability in use.

It is particularly preferred to use a continuous crimped filament tow as the fibrous component of absorbent core 1. This fiber structure has high structural integrity, and as such, is distinct from a matrix of discontinuous fibers described as fluff, or fluff pulp in the prior art. The high structural integrity enables the production of stronger webs than those formed from discontinuous fibers, which in turn are believed to enable the production of thinner absorbent pads. In addition, it is believed that the use of such fibers does not interfere with the detection of the dielectric effect of the superabsorbent particles, when compared to absorbent cores prepared by dispersing SAP particles in significant amounts of fluff or pulp.

The tow fiber can be any continuous or discontinuous thermoplastic filament tow fiber that is capable of being opened and used in combination with SAP in an absorbent core. Preferably, cellulose ester tow is used as the fibrous material in forming the absorbent core 1. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. A suitable cellulose ester will include the ability to absorb moisture, preferably is biodegradable, and is influenced not only by the substituent groups but also by the degree of substitution. The relationship between substituent groups, degree of substitution and biodegradability is discussed in W. G. Glasser et al, BIOTECHNOLOGY PROGRESS, vol. 10, pp. 214–219 (1994), the disclosure of which is incorporated herein by reference in its entirety.

Continuous filament tow useful in the present invention is beneficially moisture-absorbent and biodegradable. Accordingly, cellulose acetate tow is typically preferred for use in the invention. Typically, the denier per fiber (dpf) of the tow fiber will be in the range of about 1 to 9, preferably about 3 to 6. For the same weight product, filaments of lower dpf may provide increased surface area and increased moisture absorption. Total denier may vary within the range of about 20,000 to 60,000, depending upon the process used.

It is particularly preferred in the invention to use tow having crimped filaments. Tow materials having crimped filaments are typically easier to open. Separation of filaments resulting from bloom advantageously results in increased available filament surface area for superabsorbent material immobilization and increased moisture absorption. Gel blocking also may be reduced by using crimped tow in the absorbent core 1. As therefore may be understood, more crimp is typically better, with in excess of about 20 crimps per inch being usually preferred. Continuous filament, cellulose ester tow having crimped filaments with about 25 to 40 crimps per inch, is commercially available from Hoechst Celanese Corporation, Charlotte, N.C.

Any superabsorbent polymer (SAP) now known or later discovered may be used in the absorbent core 1, so long as it is capable of absorbing liquids. Useful SAP materials are those that generally are water-insoluble but water-swellable polymeric substances capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose that are modified to be carboxylated, phosphonoalkylated, sulphoxylated or phosphorylated, causing the SAP to be highly hydrophilic. Also included are water swellable polymers of water soluble acrylic or vinyl monomers crosslinked with a polyfunctional reactant. Such modified polymers also may be cross-linked to reduce their water-solubility, and such cross-linked SAPs have been found to provide superior performance in some absorbent cores. A more detailed recitation of superabsorbent polymers is found in U.S. Pat. No. 4,990,541 to Nielsen, the disclosure of which is incorporated herein by reference in its entirety.

Commercially available SAPs include a starch modified superabsorbent polymer available under the tradename SANWET® from Hoechst Celanese Corporation, Portsmouth, Va. SANWET® is a starch grafted polyacrylate sodium salt. Other commercially available SAPs include a superabsorbent derived from polypropenoic acid, available under the tradename DRYTECH® 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; and FAVOR manufactured by Stockhausen Inc.

During the manufacture of absorbent cores 1 for use in absorbent garments, such as diapers, it often is advantageous to target the distribution of SAP material 2 in the absorbent core 1 to concentrate SAP material 2 in locations of the absorbent core 1 more likely to come in contact with body fluids and other liquids and to minimize SAP material 2 in locations less likely to come in contact with body fluids and liquids. To illustrate, SAP concentration curve 3 illustrates the concentration of SAP material 2 (weight/unit area or grams/meter$^2$) of the absorbent core 1 over the length of the absorbent core 1. As a result, in the embodiment shown in FIG. 1, the middle section of the absorbent core 1 generally is capable of absorbing more liquid than the surrounding end portions. Accordingly, the absorbent core 1 could be used in a diaper where point 4 is collocated at the crotch of the diaper. As a result, the SAP material 2 is maximized in the area most likely needed for liquid absorbency (i.e., the crotch) and minimized in the areas less likely (i.e., the front and back). As a result of the targeting of SAP material 2, the overall amount of SAP material 2 necessary to adequately absorb fluids can be reduced, thereby reducing the cost of manufacture of the absorbent core and of the resulting diaper.

In a preferred embodiment, the absorbent core 1 is formed using a dry process. Dry processes typically have lower operating costs than wet processes because the equipment used in dry processes typically is less complex and can run at higher line speeds. Further, dry forming processes often may be adapted for use directly on the line of conventional diaper machines. An additional benefit of dry formed composite (DFC) cores is that DFC cores generally contain little or no pulp. "Little or no pulp" in the context of the present invention denotes less than 10% by weight of pulp, based on the total weight of the absorbent core 1. Preferably, less than 5% by weight fluff or pulp is used, and most preferably, less than about 2% by weight is used in the absorbent core 1 of the present invention.

Figure 2:
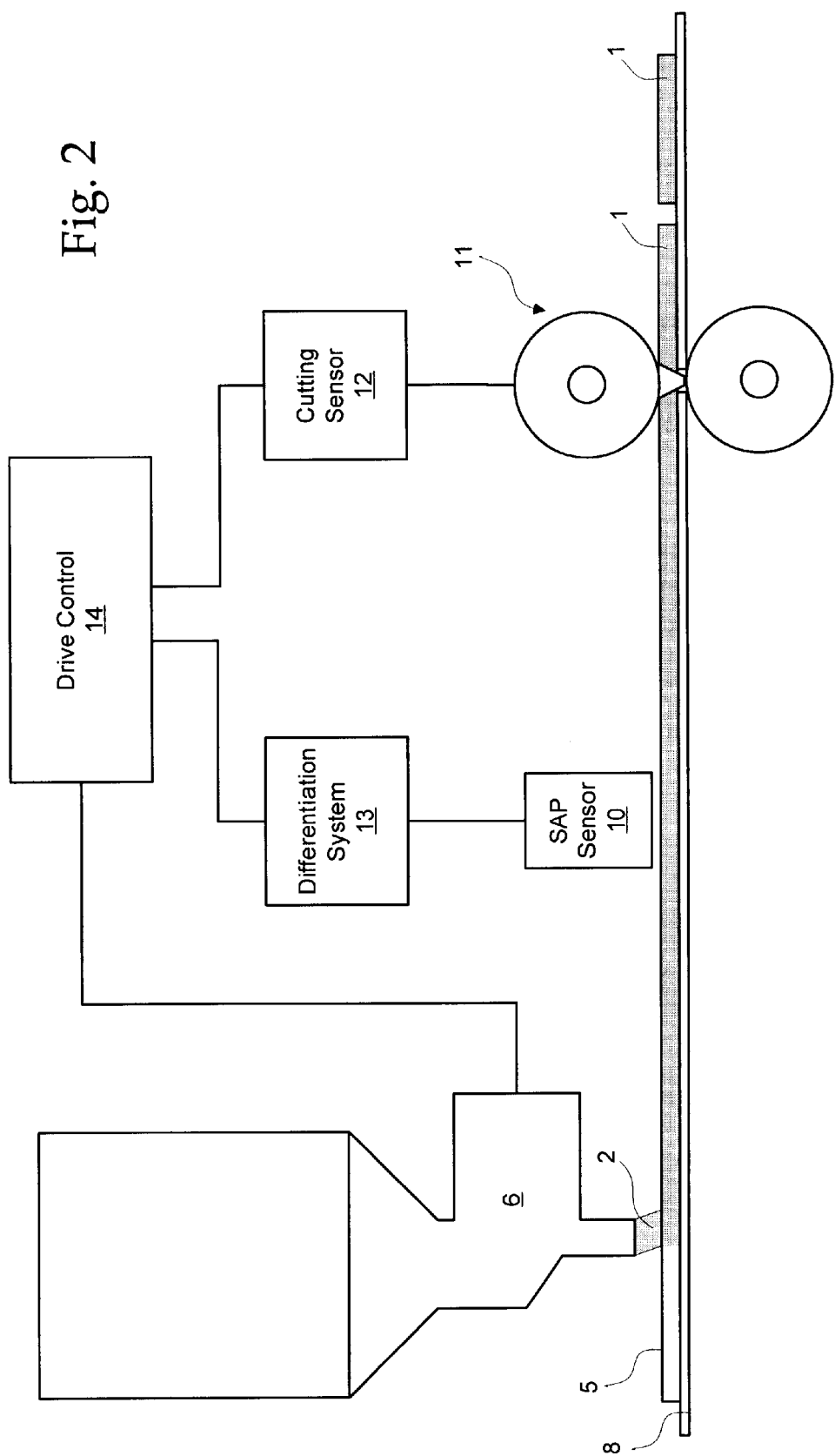
FIG. 2 includes a block diagram illustrating a system for manufacturing absorbent cores using feedback from a sensor in accordance with at least one embodiment of the present invention.

Referring now to FIG. 2, a system and a method for SAP targeting during the manufacture of dry formed composite (DFC) cores are illustrated in accordance with at least one embodiment of the present invention. In a preferred embodiment, a DFC core manufacturing system in accordance with the present invention includes a conveyor 8, a SAP targeting device 6, a cutting device 11, a SAP sensor 10, a cutting sensor 12, and a drive control 14.

In at least one embodiment, a continous sheet of DFC core material, herein referred to as core material 5, is conveyed past the SAP targeting device 6 by conveyor 8. The conveyor 8 can include any of a variety of conveyance mechanisms, such as a rotating drum, a conveyor belt, and the like. The SAP targeting device 6 distributes a SAP material 2 into segments of the core material 5 based upon a desired distribution of SAP material 2. In a preferred embodiment, the SAP targeting device 6 includes a vibratory dry material feeder. A more detailed description of a vibratory dry material feeder is found in U.S. patent application Ser. No. 10/046,280, entitled "System and Method For Depositin Particulate Matter in Absorbent Cores", and bearing attorney docket No. 53394.000549, the disclosure of which is incorporated herein by reference in its entirety. However, any of variety of SAP targeting devices may be used without departing from the spirit or the score of the present invention. After SAP material 2 is targeted into the segments of core material 5, the core material 5 is conveyed to a cutting device 11. The cutting device 11 then separates the segments of core material 5 into one or more absorbent cores 1. The absorbent cores 1 then can be incorporated into absorbent garments for use in absorbing and storing bodily fluids and other liquids.

The SAP targeting device 6 preferably targets the distribution of SAP material 2 into segments of the core material 5 by varying the concentration of the SAP material 2 within each segment of the core material 5 representing an absorbent core 1. For example, the location and concentration of SAP material 2 within the absorbent core of a diaper often differs between boy diapers and girl diapers due to the anatomical differences between male infants and female infants. By concentrating SAP material 2 in an area of the absorbent core 1 most likely to come in contact with the greatest amount of body fluids and waste, the absorbent core 1 can more efficiently absorb and store the body fluids while minimizing the amount of SAP material 2 embedded in the absorbent core 1. Those skilled in the art are capable of determining the appropriate concentration of SAP material 2 desired in the absorbent core 1 depending on the intended use of the absorbent garment, and then selecting or designing a suitable SAP targeting device 6, using the guidelines provided herein.

While it is often preferable to vary the concentration and/or placement of SAP material 2 in core material 5, variances in the timing of the SAP targeting device 6 and the cutting device 11 can result in the absorbent cores 1 having ineffectively targeted SAP material distributions. For example, relatively small differences between the timing of the cutting device 11 and the timing of the SAP targeting device 6, when compounded over time, can result in a substantial mismatch between the ideal location and concentration of SAP material 2 in an absorbent core 1 and the actual location and concentration of the SAP material 2. For example, small timing inconsistencies between the frequency that the core material 5 is cut by the cutting device 11, the feed rate of the core material 5 by the conveyor 8, and the timing of the disposition of the SAP material 2 by the SAP targeting device 6 can propagate and amplify and result in the SAP material 2 being targeted in an undesirable location of a segment of the core material 5. The present invention minimizes and/or removes completely this potential propagation and amplification problem.

Accordingly, in at least one embodiment of the invention, feedback from SAP sensor 10 is used to control the timing of the SAP targeting device 6 to compensate for variations in the timing of the cutting device 11 and/or the conveyor 8. In order to determine the current timing of the SAP targeting device 6 relative to the timing of the cutting device 11, the SAP sensor 10 is used to determine the location and/or concentration, and therefore the phasing, of SAP material 2 within the core material 5. After the SAP targeting device 6 feeds and embeds SAP material 2 into the core material 5, the core material 5 is conveyed past the SAP sensor 10, wherein the concentration of SAP material 2 at any given location along the length of a segment of the core material 5 is determined. This concentration information preferably is provided to a drive control 14 used to control the operation of the SAP targeting device 6. Similarly, the timing of the cutting device 11 is determined by a cutting sensor 12 and provided to the drive control 14. Using the SAP concentration information from the SAP sensor 10 and the cutting device timing information from the cutting sensor 12, the drive control 14 preferably modifies the operation of the SAP targeting device 6 so that the timing of the SAP targeting device 6 is synchronized with the timing of the cutting device 11. The operation of the SAP targeting device 6 can be modified preferably by changing the timing of the deposition of SAP material 2 into the corresponding segments of the core material 5. Alternatively, the operation of the SAP targeting device 6 can be modified by modifying the flow rate of SAP material 2 from the SAP target device 6, the total amount of SAP material 2 deposited in the corresponding segment of the core material 5, and the like. Skilled artisans are capable of altering the timing of a SAP targeting device using any known or later developed technique, using the guidelines provided herein.

The efficacy of known mechanisms for measuring SAP concentration of many types of absorbent cores often is limited due to properties of the absorbent cores. Many absorbent cores include a relatively high proportion of materials other than superabsorbent material, such as pulp. For example, the amount of other material in many types of absorbent cores often exceeds 50% by basis weight. Due to the manufacturing process used and the properties of these other materials, the density of these other material often varies over the length of the absorbent core material.

Because sensors used to measure the concentration of the superabsorbent material also often measure the other materials, the variance in the amount of the other materials introduces "noise" into the measurements made by the sensor. Since this noise often obscures the measurement of the concentration of superabsorbent material in the absorbent core material, any concentration measurement typically is representative of the entire concentration of the absorbent core (SAP material plus the pulp) rather than just the SAP material concentration.

However, due to the DFC core uses little or no pulp, measurement of the concentration of SAP material 2 in a DFC core generally is unaffected by the noise that typically would occur when measuring the concentration of SAP in absorbent cores containing a significant amount of fluff or pulp. Accordingly, an accurate measure of the SAP concentration in a DFC core generally is easier to obtain than with other types of absorbent cores having relatively high concentrations of pulp. Accordingly, absorbent core 1 preferably includes a DFC core, as discussed previously. However, although methods and systems for controlling the targeting of SAP are discussed in detail subsequently with reference to DFC cores, the present invention can be applied to the manufacture of other types of absorbent cores, as appropriate. Accordingly, any reference to a DFC core or DFC core material also applies to other types of absorbent cores and core materials unless otherwise noted.

It will be appreciated that it generally is desirable to use a non-destructive method to measure the concentration of SAP material 2 in the core material 5. Accordingly, the SAP sensor 10 preferably includes a sensor that is capable of measuring the changes in the dielectric effect of the core material 5 caused by changes in the concentration of SAP material 2 as the core material 5 is conveyed past the SAP sensor 10. Since the magnitude of the change in the dielectric effect due to varying concentrations of many types of SAP materials is relatively large compared to magnitude of the change in the dielectric effect caused by the varying density of other materials in the core material 5, such as fibrous tow, the change in the dielectric effect of the core material 5 from one location to another location can be correlated to the change in the concentration of the SAP material 2 in the core material 5.

To measure the dielectric effect of the core material 5, the SAP sensor 10 can include any of a variety of dielectric sensors known to those skilled in the art. Likewise, since the dielectric effect of a material is directly related to the capacitive effect of the material, the capacitive effect of core material 5 can be measured to obtain a value representative of the dielectric effect of the core material 5. Mechanisms to measure the dielectric effect and/or capacitive effect of materials are well known to those skilled in the art. Exemplary mechanisms for measuring a dielectric effect/ capacitive effect of a medium are described in U.S. Pat. No. 5,532,604 issued to Nagata and U.S. Pat. No. 5,451,882 issued to Wakino, et al., the disclosures of each of which are herein incorporated by reference in their entirety and in a manner consistent with this disclosure.

Although the SAP sensor 10 preferably includes an apparatus or device to measure the change in the dielectric effect of the core material 5 caused by a change in the concentration of SAP material 2, other non-destructive methods of measuring the concentration, or the change in concentration, of SAP material 2, can be implemented without departing from the spirit or the scope of the present invention. For example, the SAP sensor 10 can include any of a variety of sensors, such as an optical sensor to measure the permitivity of the core material 5 at a given location, an X-ray sensor, and the like. Skilled artisans are capable of designing a suitable apparatus that can measure the concentration of SAP material 2 in core material 5, and hence measure changes in the concentration of SAP material 2, using the guidelines provided herein. For clarity, the preferred embodiment wherein the dielectric effect of the core material 5 is measured to obtain the concentration of SAP material within the absorbent core material 5 is discussed. However, the present invention may be implemented using other mechanisms capable of measuring the SAP material concentration with minimal modification using the guidelines provided herein.

Instead of, or in addition to, providing information regarding a change in the concentration of SAP material 2 over the length of a segment of the core material 5 to the drive control 14, in one embodiment, a rate-of-change in the concentration over the length of the segment is provided. By using a rate-of-change in the SAP concentration rather than the absolute change, the drive control 14 can made less sensitive to variances in the dielectric effect of the core material 5 caused by factors other than a change in the concentration of SAP material 2. Some examples of these variances can include the presence of static charge, dust on the sensing equipment, changes in humidity, and the like. Because these variances generally only affect to a measurable degree the absolute measured dielectric effect, the effects of these types of variances are generally eliminated or minimized when the rate-of-change in the concentration is considered. For example, a first batch of absorbent cores 1 having a higher overall SAP material concentration could be produced. In a subsequent batch, a second batch of absorbent cores 1 having a lower overall SAP material concentration could be produced. Although the measured dielectric effect of the first batch differs from the measured dielectric effect of the second batch since more SAP material 2 is placed into each absorbent core 1 in the first batch compared to the second, the rate-of-change of the dielectric effect should be the same if the rate-of-change in the SAP material 2 deposited in each batch of absorbent cores 1 is the same. Since, in this case, the drive control 14 uses the rate-of-change of the dielectric effect rather than the change in dielectric effect, the operation of the drive control 14 with regard to controlling the phasing of the SAP targeting device 6 generally would not need modification between the first batch and the second batch.

To determine the rate-of-change of the dielectric effect, the changing dielectric effect of the core material 5 is measured by the SAP sensor 10 and provided to a differentiation system 13. The differentiation system 13 determines the rate-of-change in the dielectric effect and supplies this rate-of-change to the drive control 14, where it is compared with the timing information of the cutting device 11 from the cutting sensor 12. Based on this comparison, the drive control 14 then can adjust the timing of the SAP targeting device 6 as necessary. The differentiation system 13 can include any device capable of determining the rate-of-change in the dielectric effect, such as a low pass resistor-capacitor (RC) filter.

By comparing the timing of the distribution of SAP material 2 and the timing of the cutting device 11, the distribution of SAP material 2 by the SAP targeting device 6 can be modified to synchronize the SAP targeting device 6 with the cutting device 11. The absorbent cores 1 can be generated having the proper concentration and/or location of SAP material 2, therefore reducing or eliminating the number of absorbent cores 1 that would be rejected as a result of undesirable placement or concentrations of SAP material 2.

Figure 3:
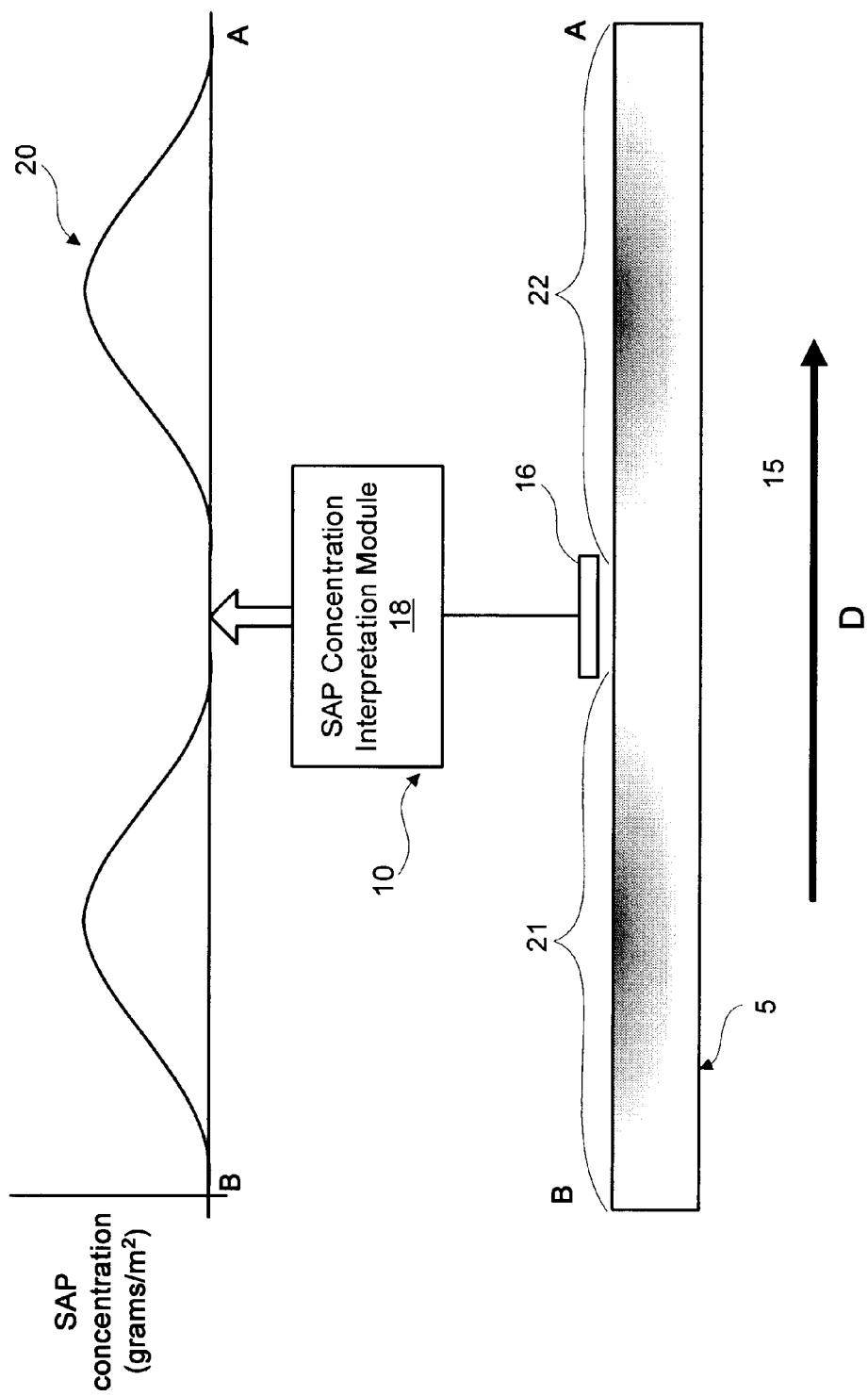
FIG. 3 includes a diagram illustrating a method for measuring a dielectric effect of a superabsorbent material to determine a concentration of the superabsorbent material in accordance with at least one embodiment of the present invention.

Referring to FIG. 3, the SAP sensor 10 is illustrated in accordance with a preferred embodiment of the present invention. As discussed previously, the SAP sensor 10 preferably includes a sensor that can measure the concentration of SAP material 2 in core material 5 by measuring the dielectric effect and/or capacitive effect of an area of the core material 5. Apparatuses capable of measuring the dielectric/capacitive effect of a material are well known to those skilled in the art. An example of such a device includes a moisture sensor available under the designation DMS3010 from Scepter Scientific, Inc. of Dublin, Calif.

As the core material 5 passes by a probe 16 of the SAP sensor 10 from point A to point B (indicated by direction D), the changing concentration of SAP material 2 results in a corresponding change in the dielectric effect caused by the SAP material 2 in a certain area of the core material 5. In one embodiment, this change in the dielectric effect is measured by the probe 16 and provided to a SAP concentration interpretation module 18 that determines a corresponding SAP concentration value, such as the weight of SAP material 2 per square meter. In another embodiment, the output of the probe 16 is provided to the drive control 14 and the drive control 14 interprets the current reading to determine the SAP concentration for the corresponding locations of the core material 5 based on the magnitude of the measured dielectric effect of the corresponding locations.

The SAP concentration signal 20 illustrates the measurement of SAP concentration in the core material 5 by the SAP sensor 10 as the core material 5 moves from point A to point B relative to probe 16. The abscissa of signal 20 represents the length of segments 21 and 22 of the core material 5 and the ordinate of signal 20 represents the SAP concentration at each corresponding point along the lengths of segments 21–22. With reference to FIG. 3, as the concentration of SAP material 2 within segments 21–22 increases, so does the measured SAP concentration value in signal 20, and vice versa. As discussed in greater detail below, the information represented by signal 20 (or its derivative), in conjunction with the phasing of the cutting device 11, can be used to control the synchronization of the SAP targeting device 6 with the cutting device 11.

As noted previously, core material 5 preferably includes DFC core material since DFC core material generally contains little or no pulp, and therefore is better suited for measuring SAP concentrations using the dielectric effect. As noted above, significant amounts of pulp can introduce noise into the measurement of the change in the dielectric effect along the length of a segment of the core material 5. Likewise, because the SAP material 2 has a high moisture content (typically about 5% by weight), the change in the concentration of the SAP material 2 generally can be determined from the change in the concentration of moisture in the core material 5. Accordingly the SAP sensor 10 preferably includes a dielectric sensor that is adapted to measure a change in dielectric effect resulting from a change in moisture of the core material 5. Such a sensor can include a dielectric sensor that preferably measures the dielectric effect of the core material 5 at frequencies in the microwave spectrum (approximately 1 gigahertz to 1 terahertz), and more preferably at about 2.5 gigahertz (the frequency at which radio waves typically are absorbed by water). Although a preferred embodiment of the SAP sensor 10 has been discussed, the SAP sensor 10 can include other types of sensors that can be adapted to measure the concentration of SAP material 2 in the core material 5, such as an X-ray transmittance sensor, an optical transmittance sensor, and the like, without departing from the spirit or the scope of the present invention.

Figure 4:
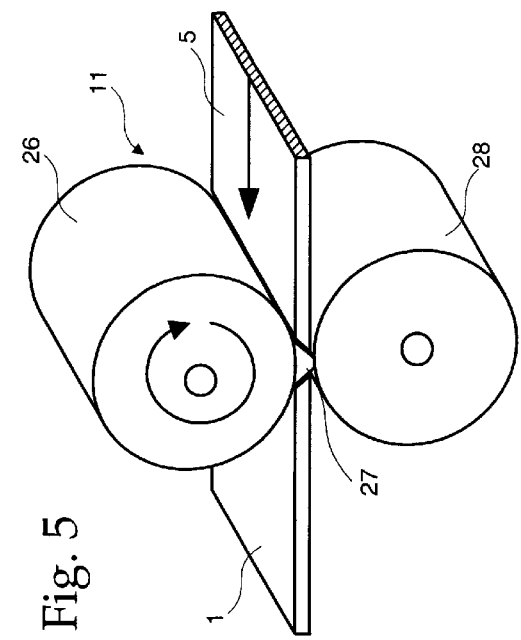
FIGS. 4–6 include isometric views illustrating the operation of a cutting device in accordance with at least one embodiment of the present invention.
Figure 5:
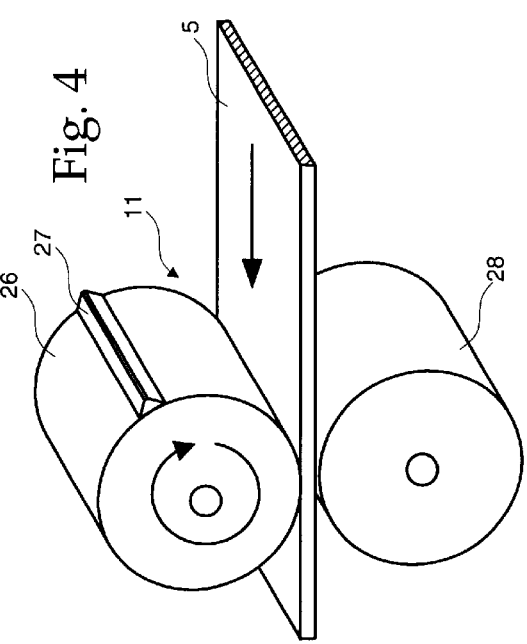
Figure 6:
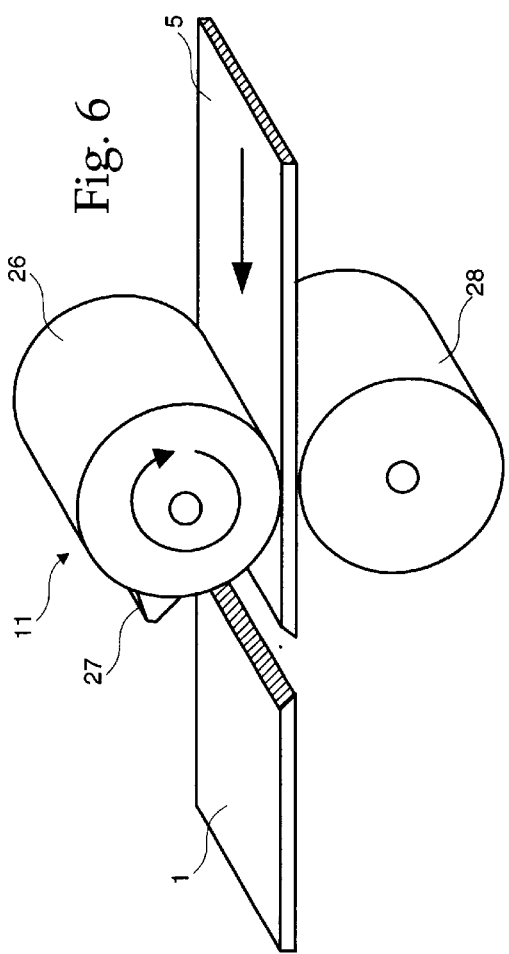

Referring now to FIGS. 4–6, the cutting device 11 is illustrated in greater detail in accordance with a preferred embodiment of the present invention. As discussed previously, the cutting device 11 is used to separate a continuous core material 5 into one or more absorbent cores 1 that then can be implemented in absorbent garments such as diapers. In a preferred embodiment, the cutting device 11 includes a cutting drum 26 having a pad knife 27 mounted longitudinally along the surface of the cutting drum 26 and a second drum 28 in parallel longitudinally with the cutting drum 26. As the core material 5 is fed past the cutting device 11 in a direction perpendicular to the longitudinal axis of the drums 26 and 28, the cutting drum 26 rotates along the longitudinal axis. As the cutting drum 26 rotates, the pad knife 27 cyclically pinches an area of the core material 5 against the second drum 28 and thereby separates, or cuts, the absorbent core 1 from the remaining core material 5.

FIG. 4 illustrates a position of the cutting drum 26 prior to cutting the core material 5. The pad knife 27 is being rotated toward the core material 5. FIG. 5 illustrates the position of the cutting drum 26 as the core material 5 is cut. In this position, the pad knife 27 pinches a segment of the core material 5 against the second drum 28 and severs the core material 5 at the edge of the segment to separate the absorbent core 1 from the remaining core material 5. FIG. 6 illustrates a position of the cutting drum 26 after cutting the core material 5. In this position, the pad knife 27 is being rotated away from the core material 5. The cutting process illustrated in FIGS. 4–6 can be repeated to generate a plurality of absorbent cores 1 from the core material 5.

Figure 7:
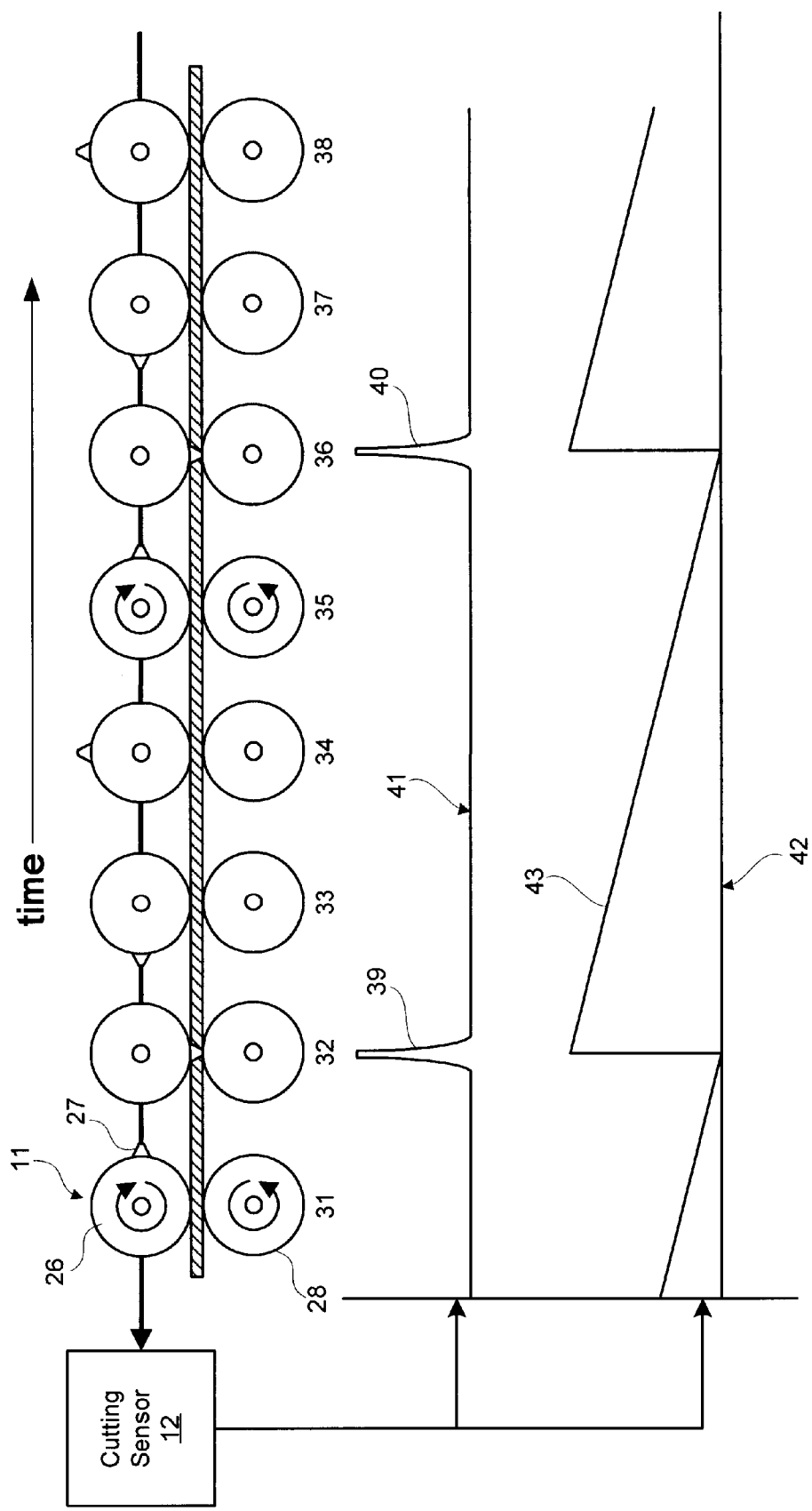
FIG. 7 includes a diagram illustrating a method for measuring a timing of a cutting device in accordance with at least one embodiment of the present invention.

Referring to FIG. 7, a method for determining the timing of the cutting device 11 is illustrated in accordance with at least one embodiment of the present invention. As discussed previously, in one embodiment, the cutting device 11 includes a cutting drum 26 having a longitudinally-mounted pad knife 27, where the cutting drum 26 rotates about its longitudinal axis to cut the core material 5 against a second drum 28. The cutting sensor 12 can be used to determine the position of the pad knife 27 with respect to the core material 5 during a cutting cycle.

As illustrated in FIG. 7, positions 31 and 35 illustrate the cutting drum 26 as it is rotating the pad knife 27 toward the core material 5; positions 32 and 36 illustrate the position of the cutting drum 26 as the pad knife 27 cuts the core material 5 to generate an absorbent core 1; positions 33 and 37 illustrate the cutting drum 26 as it is rotating away from the core material 5; and positions 34 and 38 illustrate the position of the cutting drum 26 when the pad knife 27 is in an position opposite of the cutting position.

In one embodiment, the cutting sensor 12 includes a switch, such as a programmable limit switch, that switches on when cutting drum 26 reaches the cutting position (positions 32 and 36), thereby generating a signal spike, such as the cut spike 39 of timing graph 41 corresponding to position 32 and the cut spike 40 corresponding to position 36. Alternatively, in another embodiment, the cutting sensor 12 may include a switch or sensor whose properties are modified as the cutting drum 26 changes position. As illustrated with timing graph 42, the cutting sensor 12 could include a potentiometer that generates a ramp signal 43 as the cutting drum 26 rotates about its longitudinal access. At position 32, the resistive value of the potentiometer is at a minimum, causing a maximum amplitude in ramp signal 43. As the cutting drum 26 rotates from position 32 to position 36, the resistive value of the potentiometer increases, thereby reducing the corresponding amplitude in the ramp signal 43 until position 36 is reached, whereby the resistive value of the potentiometer is reset to the minimum value and the cycle repeats. Although the cutting sensor 12 preferably includes a programmable limit switch, those skilled in the art can implement other devices to time the operation of the cutting device 11 using the guidelines provided herein.

Although methods to determine the timing of a preferred embodiment of the cutting device 11 have been discussed, the previous discussion can also be applied to other embodiments of the cutting device 11 with minimal modification. For example, the cutting device 11 could include a guillotine-type device that drops down to cut the core material 5 at a specified frequency. In this case, the timing of the guillotine could be determined using an appropriate cutting sensor 12 in a manner similar to the one discussed previously. Likewise, although a variety of methods to represent the timing of the cutting device 11 have been illustrated, any appropriate representation of the timing of the cutting device 11 may be used without departing from the spirit or the scope of the present invention. Using the guidelines provided herein, those skilled in the art are capable of designing a suitable cutting sensor 12 depending on the particular cutting device 11 employed.

Figure 8:
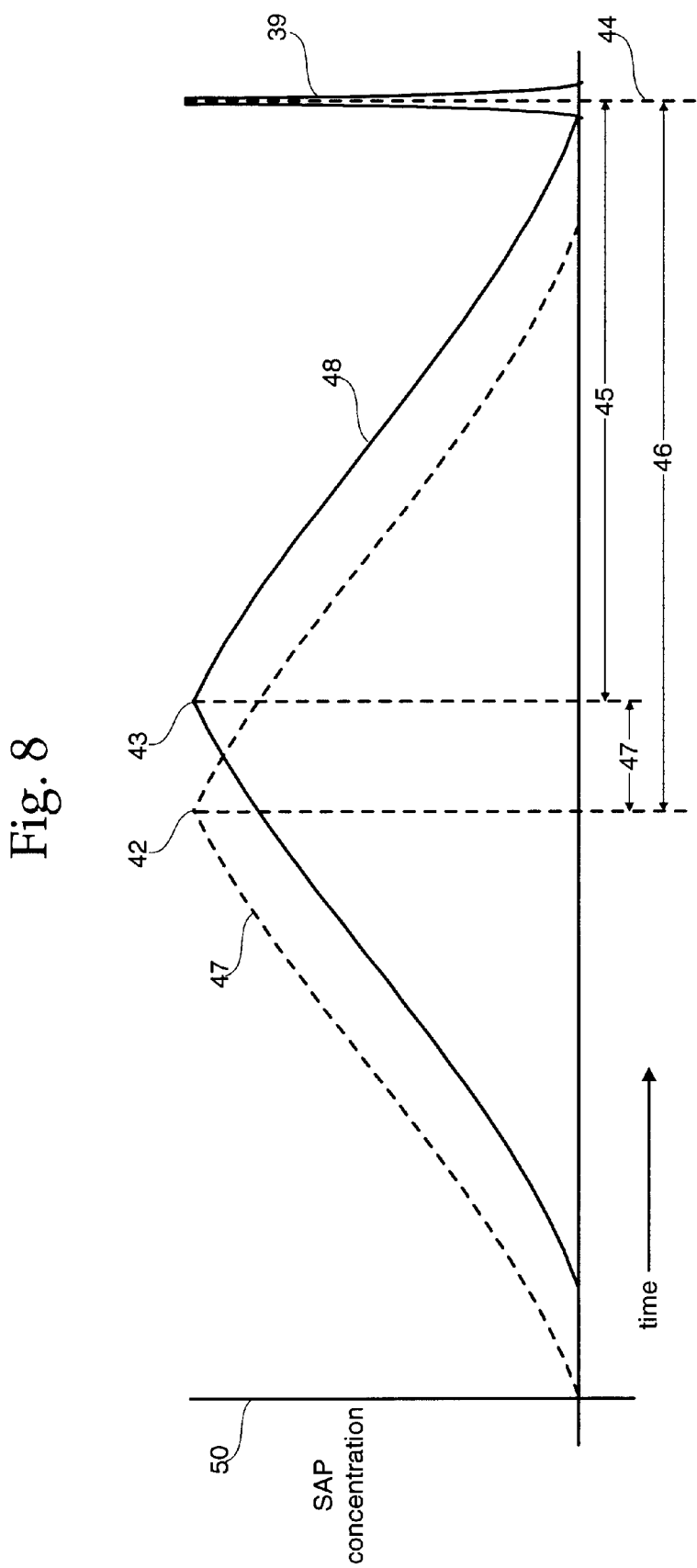
FIG. 8 includes a diagram illustrating a method for adjusting an actual targeting of superabsorbent material based on an ideal targeting in accordance with at least one embodiment of the present invention.

FIG. 8 illustrates a method for synchronizing the timing of the SAP targeting device 6 with the cutting device 11 according to at least one embodiment of the present invention. In at least one embodiment, the targeting of SAP material 2 into core material 5 is timed with respect to the timing of the cutting device 11. For example, if it is desired to concentrate the SAP material 2 within the center of the absorbent core 1, the SAP targeting device 6 times the targeting of the SAP material 2 so that it is in the middle of a segment of the core material 5 corresponding to an absorbent core 1 when cut by the cutting device 11. For example, if the core material 5 is cut every eight inches of its length to generate eight-inch long absorbent cores 1, then the SAP target area could be, in this example, centered at the fourth inch of an eight-inch long segment of core material 5, and the timing of the delivery of SAP material 5 into the segment is timed thusly.

One method of synchronizing the SAP targeting device 6 with the cutting device 11 in accordance with the present invention is to compare a theoretical timing of SAP targeting to an actual timing of SAP targeting. Since the core material 5 preferably moves from the SAP targeting device 6 to the cutting device 11 at a known and constant rate, the drive control 14 can determine, based on this constant rate and the timing of the cutting device 11, the time lapse between when a certain change in SAP concentration value is sensed by the SAP sensor 10 and when the corresponding segment of the core material 5 is to be cut by the cutting device 11 to generate an absorbent core 1. In other words, the frequency of the SAP targeting device 6 is exactly the same as the frequency of the cutting device 11, but with a constant offset so that the SAP material 2 is targeted on a portion of the core material 5 in a location in front of the location where the core material 5 is cut by the cutting device 11. Accordingly, the drive control 14 can determine this ideal time-to-cutting, herein referred to as the ideal time 45, and then compare the ideal time 45 with the actual timing 46 determined from measurements made by the SAP sensor 10. The drive control 14 can then adjust the timing of the SAP targeting device 6 to compensate for any difference between the ideal timing 45 and the actual timing 46 that exceeds a specified tolerance.

To illustrate, an ideal SAP concentration curve 47 representing an ideal change-in-SAP concentration curve over a length of a segment of the core material 5 is shown in relation to the timing of the cutting (represented by spike 39) of the segment from the core material 5 by cutting device 11 in FIG. 8. Likewise, the measured SAP concentration curve 48 illustrates the actual SAP concentration over the segment of the core material 5 as measured by the SAP sensor 10. In this example, the actual timing of the SAP targeting by the SAP targeting device 6 lagged behind the theoretical or ideal timing for SAP targeting. As a result, the targeted location of SAP material 2 is closer to the location where the core material 5 is cut (spike 39) compared to the ideal location of an ideal targeting of SAP material 2. This lag can be caused by a variety of reasons, such as a change in the composition of the SAP material 2, slippage of the core material 5 on the mechanism used to convey the core material 5, and other perturbations in the absorbent core manufacturing system. This lag could propagate to affect the timing of the targeting of SAP material 2 onto subsequent sections of the core material 5, thereby causing the SAP material 2 to be targeted in less desirable locations of the subsequent segments of the core material 5. Likewise, small errors in timing can amplify, causing unacceptable differences between the ideal timing and the actual timing. For example, small errors in timing of the SAP targeting can be compounded, resulting in the targeting of SAP material 5 in a location of the core material 5 that is bisected when the cutting device 11 cuts the core material 5.

Accordingly, in at least one embodiment, the drive control 14 uses feedback provided by the SAP sensor 10 to maintain the difference between the ideal timing of and the actual timing the SAP targeting device 6 within an acceptable range or tolerance. In at least one embodiment, the ideal timing 45 represents an ideal difference between a time when a maximum point of SAP concentration (point 42) is measured for a portion of the core material 5 and a time when the cutting device 11 is to cut the portion. For example, assume the point of maximum concentration of SAP in an absorbent core 1 ideally occurs 5 inches in front of the location that the core material 5 is cut to generate the absorbent core and the distance between the SAP sensor 10 and the cutting point of the cutting device 11 is 15 inches. Further assume that the core material 5 is moving between the SAP sensor 10 and the cutting device at a rate of 5 inches per second. Based on these assumptions, the ideal timing 45 could be calculated to be 2 seconds before the spike 39. In other words, in this example, the SAP targeting would be ideal if the maximum SAP concentration (point 42) for a portion of the core material 5 is measured at a point in time 2 seconds prior to the cutting of the portion. At t=0 seconds, point 42 is 15 seconds from the cutting point. Traveling at a rate of 5 inches/second, point 42 is 5 inches from the cutting point 2 seconds later (t=2) when the portion is cut, as desired.

Using this ideal timing 45, the drive control 14 can obtain the actual timing 46 and determine a difference 49, if any, between the actual and ideal timing of the SAP targeting device 6. Using the previous example, if the difference 49 between the timing of the maximum SAP concentration (actual timing 46) of the actual SAP concentration curve 48 and the timing of the ideal maximum SAP concentration (ideal timing 45) is 0.5 seconds, the drive control 14 can determine that the timing of the SAP targeting device 6 is 0.5 seconds fast. Accordingly, the SAP targeting device 6 could then direct the SAP targeting device 6 to adjust its timing by 0.5 seconds.

In some systems, hysteresis and temporary perturbations can cause unforeseen problems unless some leeway or tolerance is allowed between the ideal timing and the actual timing of the SAP targeting system 6. For example, the timing of the SAP targeting device 6 could temporarily be less than ideal due to a momentary stoppage in the feeder 7 connected to the SAP targeting device 6. Accordingly, if the drive control 14 were to attempt to compensate for this temporary discrepancy in timing, the drive control 14 could actually overcompensate and cause an error in the timing in the other direction. In attempting to compensate for the overcompensation, the drive control 14 could then overcompensate again, and so on, potentially causing the timing of SAP targeting by the SAP targeting device 6 to oscillate. Accordingly, to minimize the affect of hysteresis and/or the effort expended to control the timing of the SAP targeting device 6, in one embodiment, the drive control 14 preferably modifies the timing of SAP targeting device 6 only after a predetermined tolerance has been exceeded. For example, the drive control 14 could use a tolerance of 5% of the ideal timing 45 to determine if the timing of the SAP targeting device 6 should be modified. In this case, if the difference 49 between the ideal timing 45 and the actual timing 46 is less than this tolerance, then the drive control 14 can consider the timing of the SAP targeting device 6 to be within tolerance and thereby refrain from adjusting the timing of the SAP targeting device 6. On the other hand, when the difference 49 is greater than the tolerance, then the drive control 14 can modify the timing of the SAP targeting device 6 accordingly.

Figure 9:
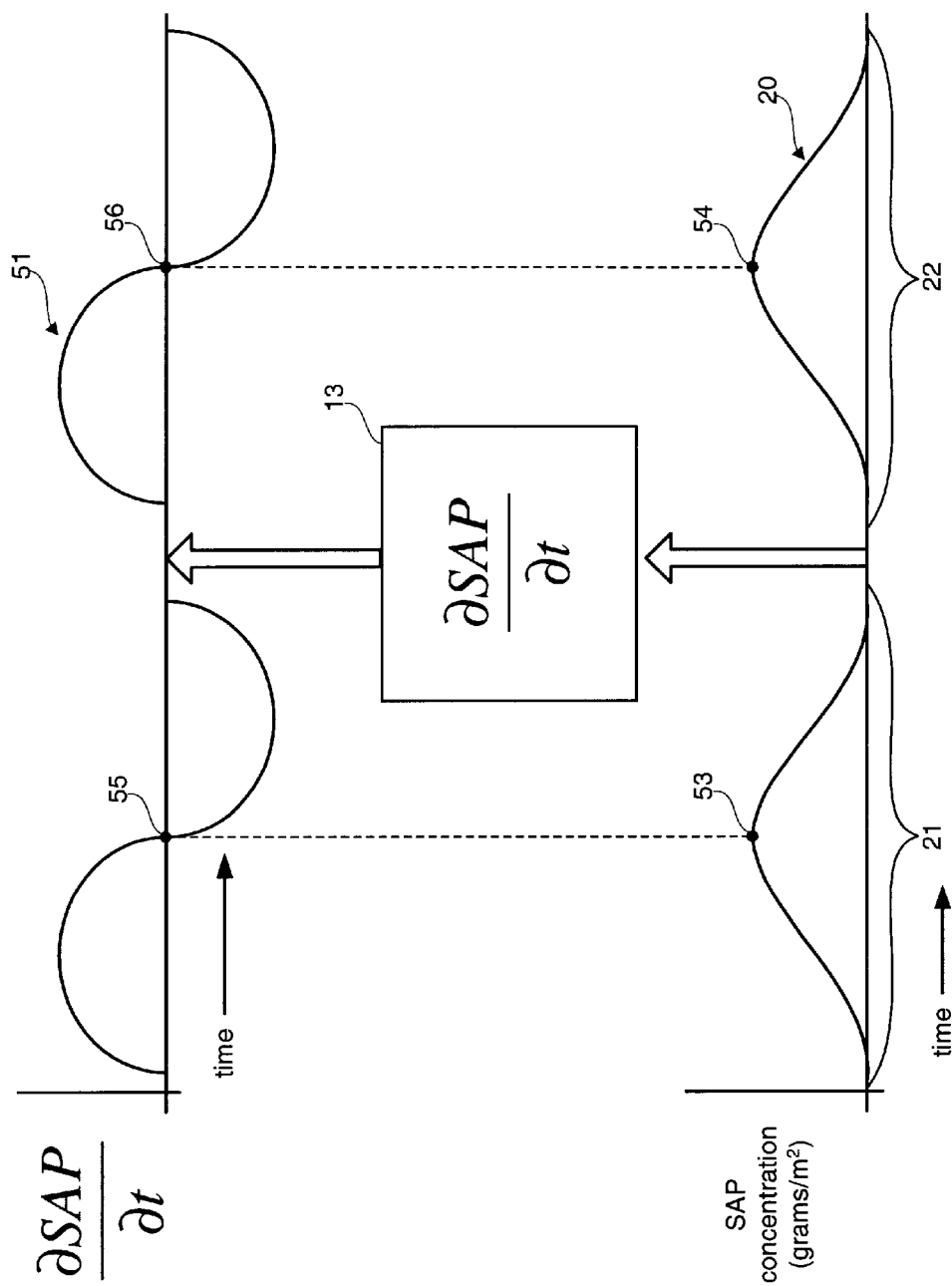
FIG. 9 includes a diagram illustrating a method for determining a rate-of-change in a concentration of superabsorbent material in an absorbent core material in accordance with at least one embodiment of the present invention.
Figure 10:
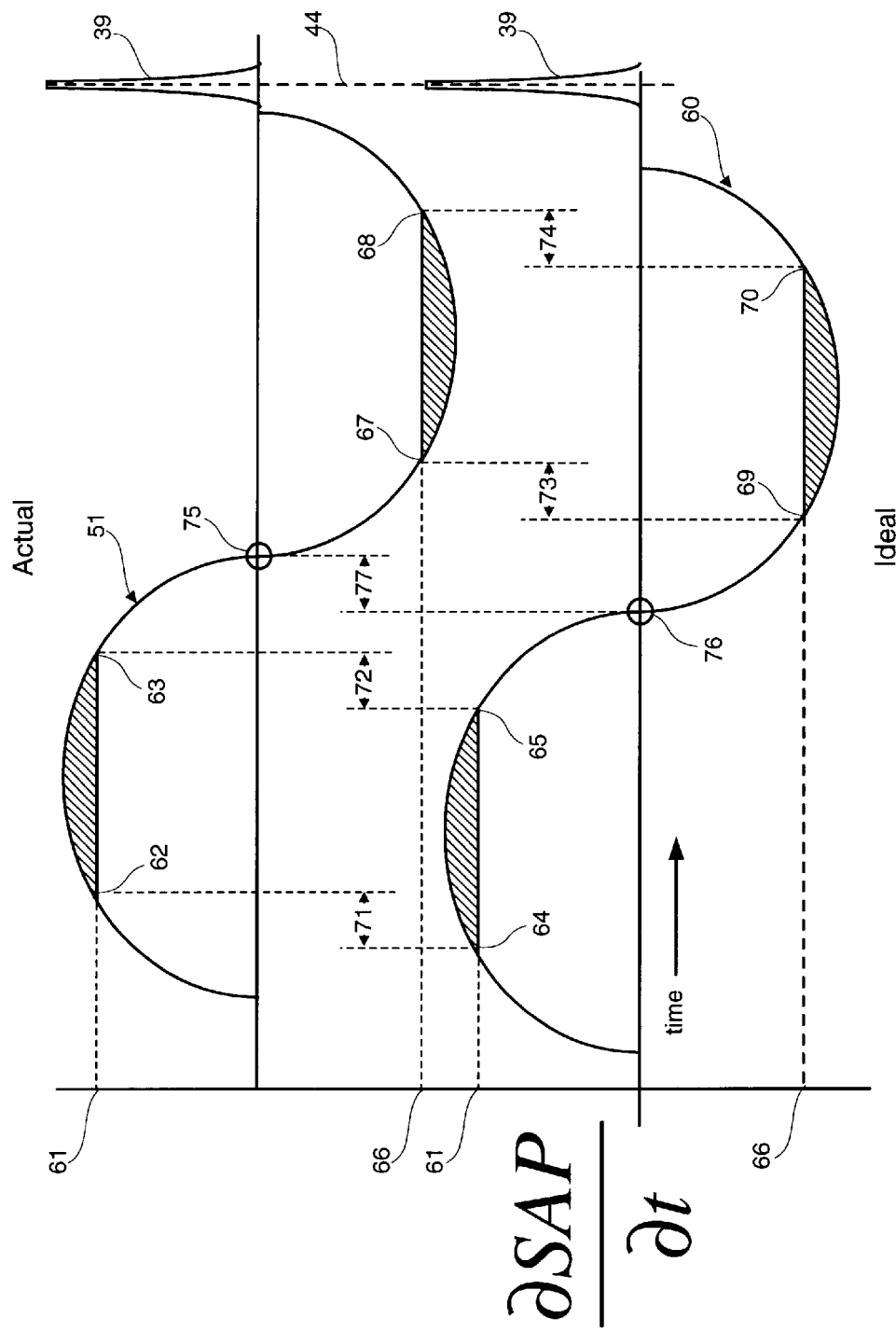
FIG. 10 includes a diagram illustrating a method for adjusting an actual targeting of superabsorbent material based on a measured rate-of-change in a concentration of superabsorbent material in accordance with at least one embodiment of the present invention.

Referring now to FIGS. 9 and 10, a method of modifying the timing of the SAP targeting device 6 based on a measured rate-of-change in the SAP concentration is illustrated in accordance with at least one embodiment of the present invention. As discussed previously, instead of, or in addition to, using the measured change in the SAP concentration over a length of a segment of the core material 5, the drive control 14 preferably uses the rate-of-change in the SAP concentration to adjust the timing of the SAP targeting device 6. Variations or noise in the signal representing the SAP concentration measured by the SAP sensor 10 can make it difficult for the drive control 14 to compare the measured signal with an ideal SAP targeting. These variances can be caused by changes in the placement of the SAP sensor, dust on the core material 5 and/or the SAP sensor 10, changes in humidity that affect the dielectric properties of the SAP material 2, static charge caused by movement of the fibrous core material 5, and the like.

Accordingly, in at least one embodiment, the SAP concentration measurement obtained by the SAP sensor 10 is converted to a measurement of the rate-of-change in the SAP concentration by, for example, a differentiation system 13 (FIG. 2) and provided to the drive control 14. The measured SAP concentration signal 20 obtained by the SAP sensor 10 as it passes over the length of two segments 21–22 of the core material 5 (as discussed with reference to FIG. 3) is provided to a differentiation system 13. The differentiation system 13 preferably determines the rate-of-change of the SAP concentration signal 20 (i.e., takes the derivative of SAP concentration signal 20) to generate differentiated SAP signal 51 and provides the differentiated SAP signal 51 to the drive control 14 for use in determining the timing of the SAP targeting device 6.

As illustrated, the differentiated SAP signal 51 represents the rate-of-change of the SAP concentration signal 20. For example, the points where the SAP concentration are at a maximum (points 53–54) in SAP concentration signal 20 are the values (points 55–56) of the differentiated SAP signal 51 where the rate-of-change transitions from a positive rate to a negative rate. Since the differentiated SAP signal 51 is independent of the absolute SAP concentration and dependent only on the rate-of-change of the SAP concentration, the differentiated SAP signal 51 is less affected, if at all, by the variations that can alter the absolute values of SAP concentration in SAP concentration signal 20.

As illustrated with reference to FIG. 10, the actual, or measured, differentiated SAP signal 51 can be used by the drive control 14 to modify the timing of the SAP targeting device 6 in a manner similar to the one discussed previously with reference to FIG. 8. As with the previous method, the drive control 14 can determine an ideal differentiated SAP signal 60 with reference to the timing of the cutting of the corresponding segment (spike 39), and compare the timing associated with the ideal differentiated SAP signal 60 with the timing of the actual differentiated SAP signal 51. In one embodiment, the timing of an occurrence of a rate-of-change value in the ideal differentiated SAP signal 60 is compared with the timing of the occurrence of the rate-of-change value in the actual differentiated SAP signal 60. To illustrate, the timing of a first (point 64) or second (point 65) occurrence of the rate-of-change value 61 in the ideal differentiated SAP signal 60 is compared to the timing of the corresponding first (point 62) or second (point 63) occurrence of the rate-of-change value 61 in the actual differentiated SAP signal 51. The difference is represented by timing difference 71 between points 62 and 64 or timing difference 72 between points 63 and 65. Similarly, timing differences 73 and 74 can be determined by comparing the first occurrences (points 67 and 69) or the second occurrences (points 68 and 70) for rate-of-change value 66. One or more of the timing differences 71–74 can then be used by the drive control 14 to modify the timing of SAP targeting by the SAP targeting device 6 to bring the SAP targeting device 6 in phase with the cutting device 11. For example, if the timing difference 71 indicates that the SAP targeting device 6 is targeting SAP material 2 0.1 seconds behind the ideal timing for SAP targeting, then the device control 14 can direct the SAP targeting device 6 to shift its timing of SAP targeting by 0.1 seconds sooner so that the actual timing of the SAP targeting more closely resembles the ideal timing for SAP targeting.

Although, as discussed previously, a variety of rate-of-change values can be used to evaluate timing differences between an ideal SAP targeting and the actual SAP targeting, a rate-of-change value of approximately zero is preferably used due to certain beneficial properties. As discussed previously with reference to FIG. 8, in one embodiment, the actual, or measured, timing of the SAP targeting device 6 is compared with an ideal timing based on a timing of a measured and ideal maximum SAP concentration rate. In many instances, it may be difficult to determine a maximum SAP concentration without differentiating the SAP concentration signal to obtain a rate-of-change of the SAP concentration. Since a maximum SAP concentration is occurs where the rate-of-change in the SAP concentration has a value of zero, the drive control 14 can more easily determine the location of maximum SAP concentration based on this zero value. Accordingly, the drive control 14 can compare the point 76 where the rate-of-change of the ideal differentiated SAP signal 60 is valued at zero with the point 75 where rate-of-change of the actual differentiated SAP signal 51 is valued at zero. This difference, represented by the timing difference 77 can then be used by the drive control 14 to adjust the timing of the SAP targeting device 6 accordingly. As noted previously, in at least one embodiment, the drive control 14 adjusts the timing of targeting device 6 when the timing difference exceeds a specified tolerance.

While the invention has been described with reference to particularly preferred embodiments, other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system comprising:
a targeting device to target superabsorbent material along a length of at least one segment of an absorbent core material;
a first sensor to generate a first signal representative of a change in a concentration of superabsorbent material along the length of at least one segment, wherein the change in the concentration is representative of a timing of the targeting device;
a cutting device to separate the at least one segment from the absorbent core material to generate at least one absorbent core;
a second sensor coupled to the cutting device to obtain a second signal representative of a timing of a cutting device for separating the at least one segment from the absorbent core material; and
a drive control coupled to the first sensor, the second sensor and the targeting device, the drive control being adapted to adjust the timing of the targeting device by an amount based on a difference between the timing of the targeting device and the timing of the cutting device.

2. The system of claim 1, wherein the absorbent core material is an absorbent core in an absorbent garment.

3. The system of claim 1, wherein the superabsorbent material includes superabsorbent polymer particles.

4. The system of claim 1, wherein the targeting device includes a vibratory dry material feeder.

5. The system of claim 1, wherein the absorbent core material includes dry formed composite core material.

6. The system of claim 1, wherein the absorbent core material includes tow fibers.

7. The system of claim 1, wherein the change in the concentration of superabsorbent material along the length of the at least one segment causes a corresponding change in a dielectric effect along the length of the at least one segment.

8. The system of claim 7, wherein the first sensor is adapted to obtain a third signal representative of the change in the dielectric effect along the length of the at least one segment.

9. The system of claim 8, wherein the first sensor includes an interpretation device to convert the third signal representative of the change in the dielectric effect to the first signal representative of the change in the concentration of superabsorbent material.

10. The system of claim 1, further including a differentiation device coupled to the first sensor and the drive control to determine a rate-of-change of the concentration of superabsorbent material along the length of the at least one segment.

11. The system of claim 10, wherein the rate-of-change of the concentration of superabsorbent material is representative of the timing of the targeting device.

12. The system of claim 1, wherein the second sensor includes a programmable limit switch.

13. A system for synchronizing a timing of a targeting of superabsorbent polymer material into absorbent core material with a timing of a cutting device, the system comprising:
a targeting device to target superabsorbent polymer material into the absorbent core material;
a first sensor to obtain a measurement of a change in a concentration of the superabsorbent material over a length of a first segment of the absorbent core material, wherein the measurement is representative of a previous timing of the targeting device;
a second sensor coupled to the cutting device to determine the timing of the cutting device;
a drive control coupled to the first sensor, the second sensor and the SAP targeting device, the drive control being adapted to adjust the timing of the targeting device for a second segment of the absorbent core material;
and wherein the timing of the targeting device is adjusted by the drive control based on a comparison of the previous timing of the targeting device and the timing of the cutting device.

14. The system of claim 13, wherein the absorbent core material is an absorbent core in an absorbent garment.

15. The system of claim 13, wherein the superabsorbent polymer material includes superabsorbent polymer particles.

16. The system of claim 13, wherein the targeting device includes a vibratory dry material feeder.

17. The system of claim 13, wherein the absorbent core material includes dry formed composite core material.

18. The system of claim 13, wherein the absorbent core material includes tow fibers.

19. The system of claim 13, wherein the change in the concentration of superabsorbent polymer material along the length of the first segment causes a corresponding change in a dielectric effect along the length of first segment.

20. The system of claim 19, wherein the first sensor is adapted to obtain a signal representative of the change in the dielectric effect along the length of the first segment.

21. The system of claim 20, wherein the first sensor includes an interpretation device to convert the signal representative of the change in the dielectric effect to a signal representative of the change in the concentration of superabsorbent material.

22. The system of claim 13, further including a differentiation device coupled to the first sensor and the drive control to determine a rate-of-change of the concentration of superabsorbent material along the length of the at least one segment.

23. The system of claim 22, wherein the rate-of-change of the concentration of superabsorbent material is representative of the previous timing of the targeting device.

24. The system of claim 13, wherein the second sensor includes a programmable limit switch.

25. A method for synchronizing a timing of a targeting of superabsorbent polymer material into absorbent core material with a timing of a cutting device, the method comprising:
determining a timing of a cutting device used to separate a first segment of an absorbent core material from a remaining portion of the absorbent core material to thereby generate an absorbent core;
determining an ideal timing of a targeting device used to target superabsorbent material along a length of the first segment of the absorbent core material before the first segment is separated by the cutting device, wherein the ideal timing is relative to the timing of the cutting device;
determining an actual timing of the targeting device, wherein the actual timing is based on a measurement of a change in concentration of superabsorbent material along the length of the first segment; and adjusting the actual timing of the targeting device for a second segment of the absorbent core material by an amount based on the difference between the ideal timing and the actual timing of the targeting device.

26. The method of claim 25, wherein the absorbent core material is an absorbent core in an absorbent garment.

27. The method of claim 25, wherein the superabsorbent polymer material includes superabsorbent polymer particles.

28. The method of claim 25, wherein the superabsorbent polymer material is targeted using a vibratory dry material feeder.

29. The method of claim 25, wherein the absorbent core material includes a dry formed composite core material.

30. The method of claim 25, wherein the absorbent core material includes tow fibers.

31. The method of claim 25, wherein determining the timing of the cutting device includes using a programmable limit switch to determine a timing of a positioning of the cutting device.

32. The method of claim 25, wherein determining the actual change in the concentration includes measuring an actual change in a dielectric effect along the length of the first segment caused by the actual change in the concentration along the length of the first segment.

33. The method of claim 25, wherein determining the ideal timing includes determining an ideal change in a concentration of superabsorbent material along the length of the first segment.

34. The method of claim 33, wherein the difference between the ideal timing and the actual timing includes a difference between the ideal change in concentration and the actual change in concentration.

35. The method of claim 25, wherein determining the actual timing includes determining a rate-of-change in the concentration of the superabsorbent material along the length of the first segment, and wherein the rate-of-change in the concentration represents the actual timing.

36. The method of claim 35, wherein determining the ideal timing includes determining an ideal rate-of-change in a concentration of superabsorbent material along the length of the first segment.

37. The method of claim 36, wherein the difference between the ideal timing and the actual timing includes a difference between the ideal rate-of-change in concentration and the actual rate-of-change in concentration.

38. A method for feed-back control of a timing of a targeting device used to target superabsorbent material into each segment of a plurality of segments of an absorbent core material before the segment is separated from a remaining portion of the absorbent core material by a cutting device, the method comprising:
  determining an ideal timing of a targeting of superabsorbent material into each segment of the plurality of segments, wherein the ideal timing is based on a timing of the cutting device;
  measuring an actual change in a concentration of superabsorbent material over a length of a first segment of the plurality of segments;
  determining an actual timing of a targeting of superabsorbent polymer material into the first segment of the plurality of segments by the targeting device based on the actual change in concentration of superabsorbent material; and
  adjusting the timing the targeting device by a first amount for a targeting of superabsorbent polymer material into a second segment of the plurality of segments, wherein the second segment is subsequent to the first segment, and where the first amount is based on a difference between the ideal timing and the actual timing.

39. The method of claim 38, wherein the absorbent core material is an absorbent core in an absorbent garment.

40. The method of claim 38, wherein the superabsorbent material includes superabsorbent polymer particles.

41. The method of claim 38, wherein the superabsorbent material is targeted using a vibratory dry material feeder.

42. The method of claim 38, wherein the absorbent core material includes a dry formed composite core material.

43. The method of claim 38, wherein the absorbent core material includes tow fibers.

44. The method of claim 38, wherein measuring the actual change in the concentration includes measuring an actual change in a dielectric effect along the length of the first segment representative of the actual change in the concentration along the length of the first segment.

45. The method of claim 38, wherein determining the ideal timing includes determining an ideal change in a concentration of superabsorbent material along the length of the first segment.

46. The method of claim 45, wherein the difference between the ideal timing and the actual timing includes a difference between the ideal change in concentration and the actual change in concentration.

47. The method of claim 38, wherein determining the actual timing includes determining a rate-of-change in the concentration of the superabsorbent material along the length of the first segment, and wherein the rate-of-change in the concentration represents the actual timing.

48. The method of claim 47, wherein determining the ideal timing includes determining an ideal rate-of-change in a concentration of superabsorbent material along the length of the first segment.

49. The method of claim 48, wherein the difference between the ideal timing and the actual timing includes a difference between the ideal rate-of-change in concentration and the actual rate-of-change in concentration.

50. A method for synchronizing a timing of a targeting of superabsorbent polymer material into absorbent core material with a timing of a cutting device, the method comprising:
  targeting superabsorbent polymer material into a first segment of an absorbent core material using a first timing;
  obtaining a first signal representative of a change in a dielectric effect over a first segment, wherein the change in the dielectric effect is representative of an actual change in a concentration of superabsorbent polymer material over the first segment;
  determining a difference between an actual timing represented by the first signal and an ideal timing, the ideal timing representing an ideal targeting of superabsorbent polymer material into the first segment relative to a timing of a separation of the first segment from the absorbent core material;
  adjusting the first timing by the difference to generate a second timing; and
  targeting superabsorbent polymer material into a second segment of the absorbent core material using the second timing.

51. The method of claim 50, wherein the absorbent core material is an absorbent core in an absorbent garment.

52. The method of claim 50, wherein the superabsorbent polymer material includes superabsorbent polymer particles.

53. The method of claim 50, wherein the superabsorbent polymer material is targeted by a vibratory dry material feeder.

54. The method of claim 50, wherein the absorbent core material includes a dry formed composite core material.

55. The method of claim 50, wherein the absorbent core material includes tow fibers.

56. The method of claim 55, wherein the difference between the ideal timing and the actual timing includes a difference between an ideal change in concentration and the actual change in concentration.

57. A method for synchronizing a timing of a targeting of superabsorbent polymer material into absorbent core material with a timing of a cutting device, the method comprising:

targeting superabsorbent polymer material into a first segment of an absorbent core material using a first timing;

obtaining a first signal representative of an actual change in a dielectric effect over a first segment resulting from a change in a concentration of superabsorbent polymer material over the first segment;

differentiating the first signal to obtain a second signal representative of an actual rate-of-change in the concentration of superabsorbent polymer material over the first segment;

determining a difference between an actual timing represented by the second signal and an ideal timing, the ideal timing representing an ideal targeting of superabsorbent material into the first segment relative to a timing of a separation of the first segment from the absorbent core material;

adjusting the first timing by the difference to generate a second timing; and targeting superabsorbent material into a second segment of the absorbent core material using the second timing.

58. The method of claim 57, wherein the absorbent core material is an absorbent core in an absorbent garment.

59. The method of claim 57, wherein the superabsorbent polymer material includes superabsorbent polymer particles.

60. The method of claim 57, wherein the superabsorbent polymer material is targeted by a vibratory dry material feeder.

61. The method of claim 57, wherein the absorbent core material includes a dry formed composite core material.

62. The method of claim 57, wherein the absorbent core material includes tow fibers.

63. The method of claim 62, wherein the difference between the ideal timing and the actual timing includes a difference between an ideal rate-of-change in concentration and the actual rate-of-change in concentration.

\* \* \* \* \*